United States Patent
Boutami et al.

(10) Patent No.: US 10,401,282 B2
(45) Date of Patent: Sep. 3, 2019

(54) MODULAR INFRARED RADIATION SOURCE

(71) Applicant: COMMISSARIAT A L'ENERGIE ATOMIQUE ET AUX ENERGIES ALTERNATIVES, Paris (FR)

(72) Inventors: Salim Boutami, Grenoble (FR); Emerick Lorent, Crolles (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 16/167,972

(22) Filed: Oct. 23, 2018

(65) Prior Publication Data

US 2019/0120755 A1    Apr. 25, 2019

(30) Foreign Application Priority Data

Oct. 24, 2017    (FR) .................................... 17 60055

(51) Int. Cl.
*G01N 21/35*    (2014.01)
*G01N 21/17*    (2006.01)
*G01N 21/3504*    (2014.01)

(52) U.S. Cl.
CPC ..... *G01N 21/3504* (2013.01); *G01N 21/1702* (2013.01); *G01N 2021/1704* (2013.01); *G01N 2201/0691* (2013.01)

(58) Field of Classification Search
CPC .......... G01N 21/1702; G01N 21/3504; G01N 2021/1704; G01N 2201/0691
See application file for complete search history.

(56) References Cited

U.S. PATENT DOCUMENTS

| | | |
|---|---|---|
| 6,344,647 B1 | 2/2002 | Jourdain et al. |
| 6,897,551 B2 | 5/2005 | Amiotti |
| (Continued) | | |

FOREIGN PATENT DOCUMENTS

| | | |
|---|---|---|
| EP | 3 096 345 A1 | 11/2016 |
| EP | 3 153 831 A1 | 4/2017 |
| (Continued) | | |

OTHER PUBLICATIONS

French Preliminary Search Report dated Jun. 22, 2018 in French Application 17 60055 filed on Oct. 24, 2017 (with English Translation of Categories of Cited Documents).

(Continued)

*Primary Examiner* — Mark R Gaworecki
(74) *Attorney, Agent, or Firm* — Oblon, McClelland, Maier & Neustadt, L.L.P.

(57) ABSTRACT

A modular infrared radiation source is provided, including a support provided with a flat wall; a membrane including front and rear faces essentially parallel to each other, the membrane being configured to emit infrared radiation by the front and rear faces, and being maintained in suspension with respect to the support, the rear face facing the wall at a distance therefrom, the wall being configured to reflect infrared radiation; and an electrostatic actuator including first and second electrodes arranged facing each other, configured to vary the distance by application of a difference in electrostatic potential between the first and second electrodes, the membrane and the electrostatic actuator arranged such that, for each wavelength, infrared radiation emitted by the rear face is reflected by the wall, passes through the membrane from the rear face to the front face, and interferes with infrared radiation emitted by the front face.

19 Claims, 7 Drawing Sheets

(56) References Cited

U.S. PATENT DOCUMENTS

| | | | |
|---|---|---|---|
| 2010/0001361 A1 | 1/2010 | Caplet et al. | |
| 2016/0142005 A1* | 5/2016 | Bernardi | H02S 10/30 |
| | | | 136/253 |
| 2017/0102323 A1 | 4/2017 | Boutami et al. | |
| 2018/0335345 A1* | 11/2018 | Gjessing | G01J 3/108 |
| 2018/0356290 A1* | 12/2018 | Winger | G01J 5/061 |

FOREIGN PATENT DOCUMENTS

| | | |
|---|---|---|
| WO | WO 97/049109 A1 | 12/1997 |
| WO | WO 2009/087284 A1 | 7/2009 |
| WO | WO 2013/167874 A1 | 11/2013 |
| WO | WO 2017/060264 A2 | 4/2017 |

OTHER PUBLICATIONS

Pierre Barritault, et al., "Mid-IR source based on a free-standing microhotplate for autonomous $CO_2$ sensing in indoor applications," Sensors and Actuators A 172, 2011, pp. 379-385.

Anthony Lefebvre, "Simulation et conception de microsources infrarouges nanophotoniques pour la detection de gaz," Optique /physics.optics/ Universite Paris-Saclay, 2015, 121 Pages (with English Abstract).

* cited by examiner

MODULAR INFRARED RADIATION SOURCE

TECHNICAL FIELD

The present invention relates to a modular infrared radiation source. In particular, the invention relates to an infrared radiation source adapted to modulate, by electrostatic actuation, its infrared emission spectrum.

PRIOR ART

Non-dispersive infrared (NDIR) sources are known from the prior art, and are widely implemented in gas detectors.

As an example, FIG. 1 illustrates a micro-infrared source known from the prior art and described by Barritault et al. [1]. In particular, the micro-infrared source comprises a metal filament formed on a membrane suspended by two suspension arms.

The metal filament, when an electric current runs through it, heats up and emits an infrared radiation according to the black body law.

However, this infrared source known from the prior art is not satisfactory.

Indeed, the dynamic of starting up and/or extinguishing this type of source is based on a very slow thermal equilibrium such that the modulation frequency of said source does not exceed one kilohertz.

Also, from the moment that modulation frequencies of the order of ten or so kHzs are required, notably for the photoacoustic detection of gases, quantum cascade lasers (hereafter "QCL") are generally implemented.

However, the latter, on account of their very low efficiency (below 1%), consume too much energy.

Furthermore, QCL are generally associated with a cooling system, for example a Pelletier system, which adversely affects the bulk of the system in which they are integrated.

Finally, QCL are also very expensive.

One aim of the present invention is then to propose an infrared radiation source enabling a modulation of said radiation at frequencies being able to reach ten or so kHzs.

Another aim of the present invention is to propose an infrared radiation source not requiring the implementation of a cooling system, and consequently more compact.

DESCRIPTION OF THE INVENTION

The aims of the invention are at least in part attained by a modular infrared radiation source which comprises:
- a support provided with a flat wall;
- a membrane comprising two essentially parallel faces designated, respectively, front face and rear face, the membrane being adapted to emit an infrared radiation according to one and the other of its faces and maintained in suspension with respect to the support, the rear face being facing and at a distance D from the wall, said wall being further adapted to reflect the infrared radiation capable of being emitted by the membrane;
- electrostatic actuating means adapted to vary the distance D.

According to one embodiment, the membrane and the electrostatic actuating means are laid out such that, for each wavelength, the infrared radiation emitted by the rear face is reflected by the wall, passes through the membrane from its rear face to its front face and interferes with the infrared radiation emitted by the front face.

According to one embodiment, the membrane comprises an emissive layer which, when it is traversed by a current, heats up and emits infrared radiation.

According to one embodiment, the membrane comprises from its front face to its rear face, a front dielectric layer, the emissive layer, and a rear dielectric layer.

According to one embodiment, the electrostatic actuating means comprise two electrodes designated, respectively, first electrode and second electrode, arranged facing each other, and intended, by application of a difference in electrostatic potential between said electrodes, to vary the distance D.

According to one embodiment, the wall forms the first electrode and the second electrode is covering the rear face, the second electrode being at least partially transparent to the infrared radiation capable of being emitted by the membrane.

According to one embodiment, the second electrode is cut out such that said second electrode covers the rear face according to a coverage factor comprised between 40% and 60%.

According to one embodiment, the second electrode has at least one of the shapes selected from: a grid, a circular spiral, a rectangular spiral, a coil.

According to one embodiment, the second electrode comprises a metal species, advantageously the metal species comprises at least one of the elements selected from: copper, aluminium, tungsten, gold, platinum, silver, palladium, tantalum, molybdenum.

According to one embodiment, the second electrode wholly covers the rear face, advantageously the second electrode is made of conductive transparent oxide.

According to one embodiment, the support is a hermetically sealed enclosure, inside of which the membrane is arranged, and of which the environment is maintained at a pressure below $10^{-2}$ mbars, preferentially comprised between $10^{-3}$ mbars and $10^{2}$ mbars.

According to one embodiment, one and/or the other of the electrodes comprises a trap adapted, from the moment that it is heated, to trap at least in part gaseous species capable of being present in the enclosure, advantageously one and/or the other of the two electrodes comprises titanium and/or zirconium.

According to one embodiment, the second electrode comprises the trap.

According to one embodiment, the source further comprises a band pass filter intended to filter the infrared radiation emitted by said source.

The invention also relates to a photoacoustic gas detection device implementing the source according to the present invention.

The invention also relates to a device for detecting gases by infrared spectroscopy implementing the source according to the present invention.

The invention also relates to a method for manufacturing an infrared radiation source, the method comprising:

a) a step of formation of a membrane comprising two essentially parallel faces designated, respectively, front face and rear face, the membrane being adapted to emit an infrared radiation according to one and the other of its faces, the membrane being maintained in suspension with respect to a support, the rear face facing and at a distance D from a wall, said wall further being adapted to reflect the infrared radiation capable of being emitted by the membrane;

b) the formation of electrostatic actuating means adapted to vary the distance D;

the membrane and the electrostatic actuating means being laid out such that, for each wavelength, the infrared radiation emitted by the rear face is reflected by the wall, passes through the membrane from its rear face to its front face and interferes with the infrared radiation emitted by the front face.

According to one embodiment, the step a) comprises the formation of a stack on a first face of a support substrate, said stack being intended to form the membrane.

According to one embodiment, the support substrate is assembled with a second support substrate, the assembly being advantageously hermetic, the second support substrate comprising a cavity of which the bottom forms the wall, advantageously the wall is lined with an electrode designated first electrode.

According to one embodiment, the assembly of the support substrate and the second support substrate is followed by the formation of a through opening of the support substrate from a second face of said support substrate opposite to the first face, the formation of the through opening intended to free the membrane.

According to one embodiment, the step b) comprises the formation of a second electrode covering the membrane.

According to one embodiment, a cover is formed covering the through opening by the second face of the support substrate.

BRIEF DESCRIPTION OF THE DRAWINGS

Other characteristics and advantages will become clear in the description that follows of embodiments of the modular infrared radiation source, given as non-limiting examples, with reference to the appended drawings in which:

FIG. 6a represents the emissivity of said source in the absence of electrostatic potential applied between the two electrodes, whereas in FIG. 6b, an electrostatic potential is imposed in such a way as to displace the membrane by 250 nm;

DETAILED DESCRIPTION OF PARTICULAR EMBODIMENTS

The invention described in a detailed manner below implements a modular infrared radiation source which comprises a membrane adapted to emit an infrared radiation according to its two faces designated, respectively, front face and rear face. The membrane is, furthermore, maintained in suspension with respect to a support, the rear face being facing and at a distance D from a reflective wall of said support.

The infrared radiation source further comprises electrostatic actuating means which, by application of an electrical voltage, are adapted to vary the distance D.

Thus, according to this layout, for any wavelength λ, the infrared radiation emitted by the rear face is reflected by the wall in the direction of the membrane, passes through said membrane from its rear face to its front face and interferes with the infrared radiation emitted by the front face. The interference state for each wavelength is then dependent on the variation in distance D imposed by the electrostatic actuating means.

In FIGS. 2a to 7 may be seen an infrared radiation source 100 according to the present invention.

Figure 1:
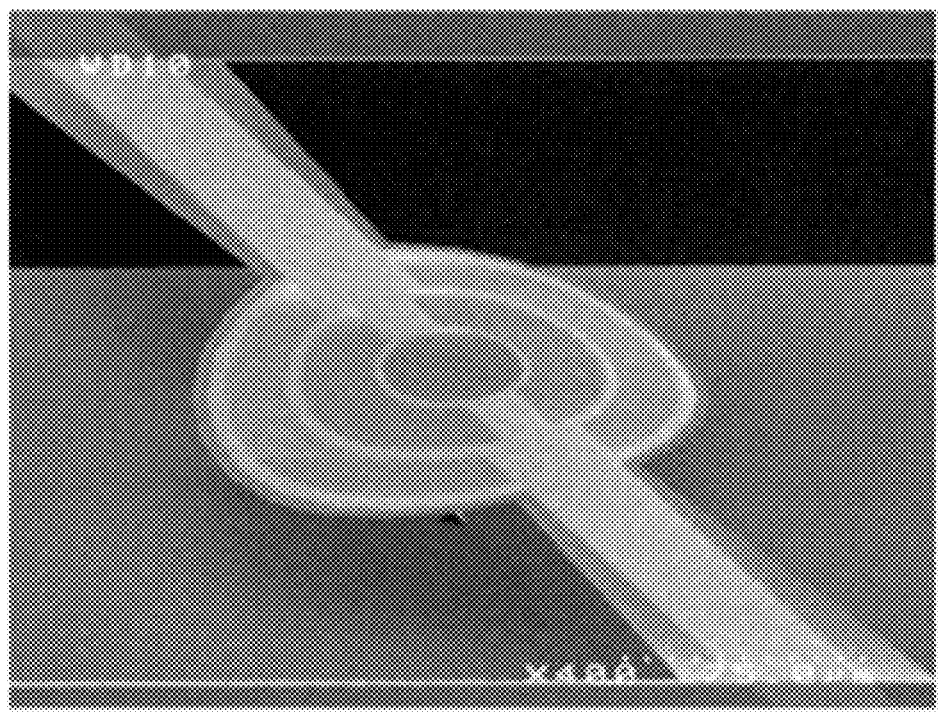
FIG. 1 is an image, obtained by microscopy, of a resistive element known from the prior art.
Figure 2A:
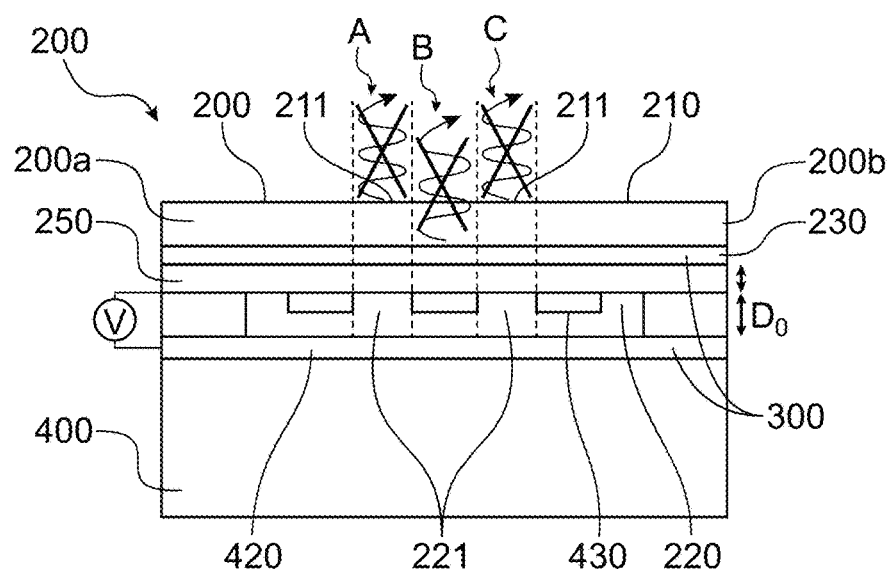
FIGS. 2a and 2b are schematic representations of a modular infrared radiation source according to the present invention along a sectional plane perpendicular to the membrane, in particular the difference in potential between the two electrodes is zero and non-zero, respectively, in FIG. 2a and in FIG. 2b.
Figure 2B:
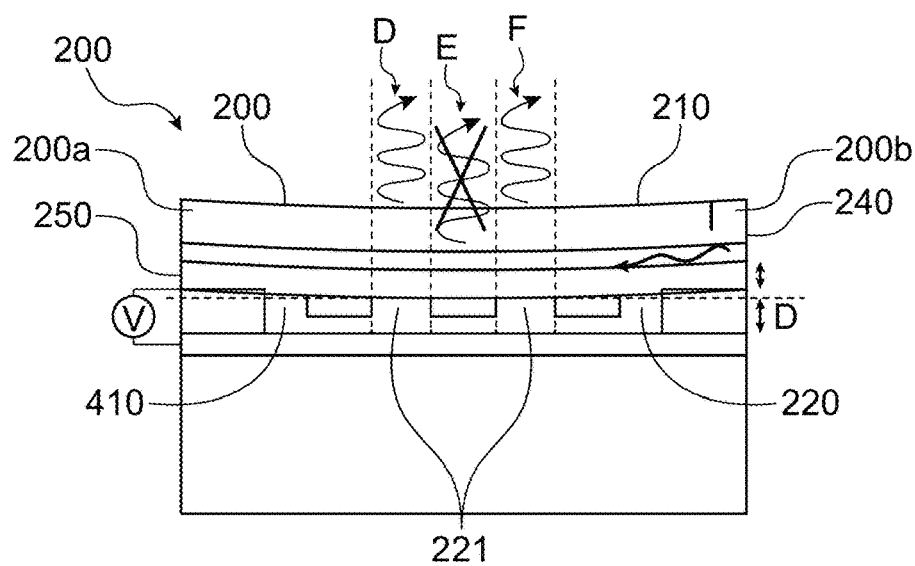

The infrared radiation source 100 comprises a membrane 200 (FIGS. 2a and 2b).

Figure 4:
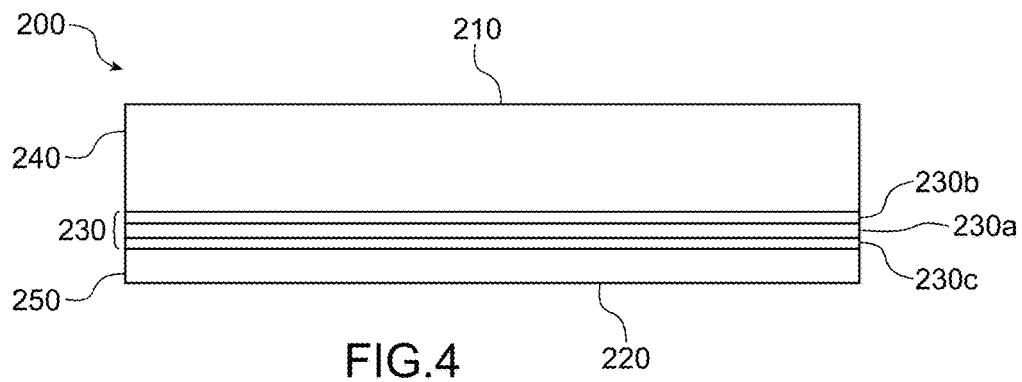
FIG. 4 is a schematic representation, along a sectional plane perpendicular to the rear face, of a membrane capable of being implemented within the scope of the present invention.

The membrane 200 comprises two essentially parallel faces designated, respectively, front face 210 and rear face 220, and is adapted to emit an infrared radiation according to one and the other of its two faces (FIGS. 2a, 2b, and 4).

The membrane 200 may be of square, rectangular, or instead circular shape.

The membrane 200 may also have a thickness comprised between 100 nm and 1 µm, in particular the membrane 200 may have a thickness of 200 nm.

"Infrared radiation" is taken to mean a light radiation in a domain of wavelengths comprised between 1 µm and 12 µm, advantageously between 3 µm and 12 µm.

Advantageously, the membrane 200 may comprise an emissive layer 230 which, when it is heated (for example when it is traversed by an electric current), produces and emits infrared radiation.

It is thus understood that the infrared radiation source 100 may comprise current generating means intended to impose the passage of a current in the emissive layer 230.

The emissive layer 230 may, for example, comprise a layer of platinum 230a of 30 nm thickness intercalated between two layers of TiN, 230b and 230c, each of 10 nm (FIG. 4).

Still advantageously, the membrane 200 may comprise, from its front face 210 to its rear face 220, a front dielectric layer 240, the emissive layer 230, and a rear dielectric layer 250 (FIGS. 2a, 2b and 4).

The front 240 and rear 250 dielectric layers may comprise at least one of the elements selected from: silicon dioxide, silicon nitride.

The front 240 and rear 250 dielectric layers may have a thickness comprised between 50 nm and 500 nm.

The infrared radiation source 100 further comprises a support 400 provided with a flat wall 410, said wall being adapted to reflect the infrared radiation capable of being emitted by the membrane 200.

According to the present invention, the term "wall" is assimilated with a face, advantageously flat.

"Adapted to reflect infrared radiation" is taken to mean a wall having a coefficient of reflection in the range of wavelengths of the infrared radiation considered above 75%, advantageously above 90%, even more advantageously above 95%.

According to the present invention, the membrane 200 is maintained in suspension with respect to the support 400, the rear face 220 facing and at a distance D from the wall 410.

"Maintained in suspension" is taken to mean a membrane 200 maintained to the support 400, for example, by two suspension arms 200*a* and 200*b* (FIGS. 2*a* and 2*b*).

The infrared radiation source 100 also comprises electrostatic actuating means 300 adapted to vary the distance D.

"Electrostatic actuator" or "electrostatic actuating means" is taken to mean means that make it possible to impose, in response to an electrostatic interaction, the relative displacement of two moveable components. Within the scope of the present invention, the electrostatic interaction may have for origin a difference in electrostatic potential imposed between a first electrode 420 and a second electrode 430 integral (FIGS. 2*a* and 2*b*), respectively, with the support 400 and with the membrane 200. The distance D for which the difference in electrostatic potential between the first electrode 410 and the second electrode 420 is zero is designated distance at zero potential $D_0$.

The difference in electrostatic potential may for example be imposed by a voltage source. It is understood that the first electrode 420 and the second electrode 430 each comprise a connection terminal at the level of which may be imposed an electrostatic potential.

The membrane 200 and the electrostatic actuating means 300 are laid out such that, for each wavelength λ, the infrared radiation emitted by the rear face 220 is reflected by the wall 410, passes through the membrane 200 from its rear face 220 to its front face 210, and interferes with the infrared radiation emitted by the front face 210.

In other words, for each wavelength λ, the infrared radiation emitted by the rear face 220 sees imposed a path difference or dephasing, with respect to the infrared radiation emitted by the front face 210, due to the distance D and to the reflection against the wall 410 (and to a lesser extent by its passing through the membrane). The interferences produced may then be constructive or destructive according to the induced dephasing.

It is understood that the aforementioned layout imposes that the rear face 220 and the wall 410 are essentially parallel with each other.

Advantageously, the wall 410 forms the first electrode 420. For example, the first electrode 420 is a layer, advantageously a metal layer. The metal layer may be an aluminium layer. The second electrode 430 (which is facing the first electrode) is, in these conditions, covering the rear face 220, and is, at least partially, transparent to infrared radiation.

"At least partially transparent to infrared radiation" is taken to mean a second electrode 430 that has a coefficient of transmission of infrared radiation above 40%, for example comprised between 40% and 60%.

According to a first embodiment, the second electrode 430 may be cut out. "Cut out electrode" is taken to mean an electrically continuous electrode and which has one or more through openings 431 (FIGS. 2*a*, 2*b* and 4*a* to 4*d*) making it possible to expose one or more rear zones 221 of the rear face 220.

The through openings 431 advantageously have a dimension above 10 μm, preferably above 50 μm.

According to this embodiment, the second electrode 430 may advantageously be made of a metal species.

Figure 3A:
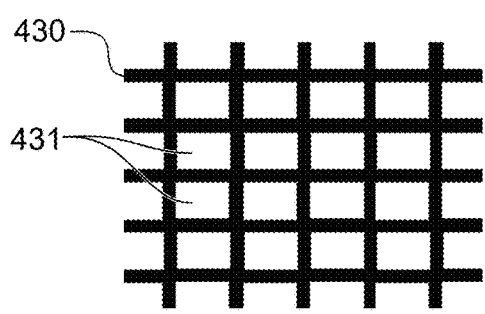
FIGS. 3a to 3d are schematic representations of second electrodes capable of being implemented in the present invention.
Figure 3C:
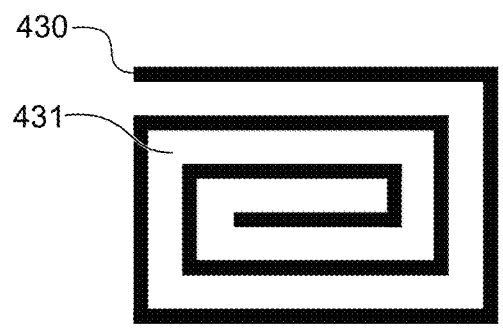
Figure 3B:
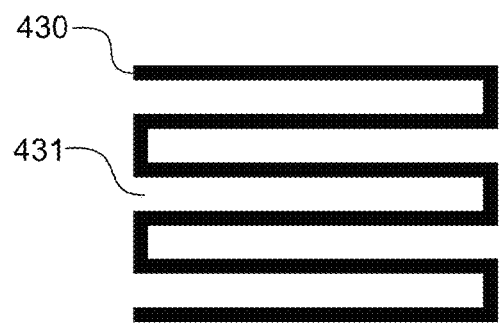
Figure 3D:
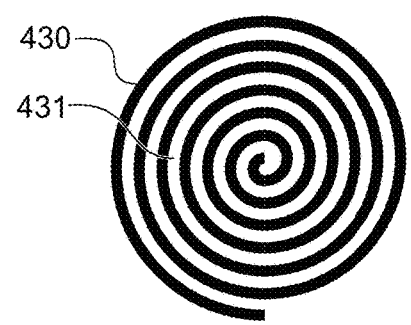

The transparency of the second electrode 430 is then adjusted by the extent of the through openings 431. In particular, FIGS. 3*a* to 3*d* represent shapes of second electrodes capable of being implemented according to the first embodiment. As represented in these figures, the second electrode may have the shape of a grid (FIG. 3*a*), a coil (FIG. 3*b*), a rectangular spiral (FIG. 3*c*), or instead a circular spiral (FIG. 3*d*). The invention is not however limited to these shapes.

Furthermore, from the moment that it is metal, the second electrode 430 may comprise at least one of the metals selected from: aluminium, copper, tungsten, gold, platinum, silver, palladium, tantalum, molybdenum.

In operation, and according to this first embodiment in which the second electrode 430 is cut out and comprises a metal species, only the rear zone or zones 221 not covered with metal, as well as the front zone or zones 211 of the front face 210 facing the rear zones 221, are capable of emitting an infrared radiation.

The other zones of the front face 210 and the rear face 220, on account of their proximity to a second metal electrode, see their infrared radiation annihilated by said electrode. The annihilation of the radiation is symbolised, in FIGS. 2*a* and 2*b*, by a radiation crossed out with a cross (marks A, C, D and F).

Thus, the infrared radiation emitted by the rear zone or zones 221, for each of its wavelengths, after reflection against the first electrode 420, passes through the membrane from its rear face 220 to its front face 210 at the level of the rear zone or zones 221 to interfere with the infrared radiation emitted at the level of the front zone or zones 211.

Figure 5:
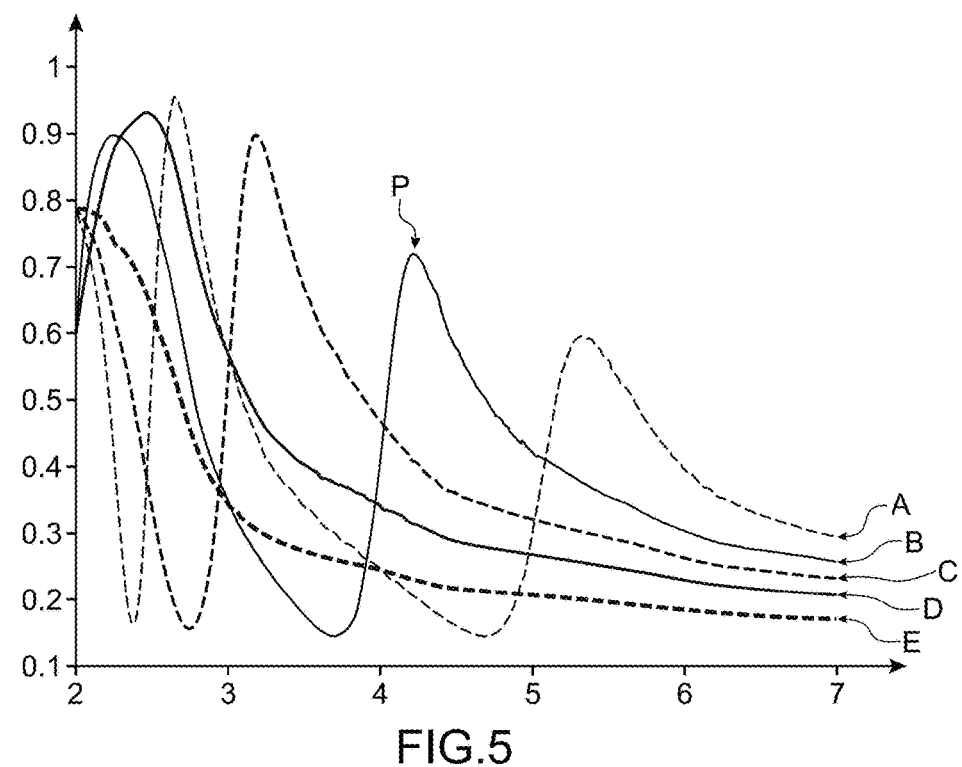
FIG. 5 is a graphic representation of the emissivity (vertical axis) of the infrared source as a function of the wavelength λ (horizontal axis) for different distances D (curve A: D=2.25 µm; curve B: D=1.75 µm; curve C: D=1.25 µm; curve D: D=0.75 µm; curve E: D=0.25 µm).

As illustrated in FIG. 5, the interference state for each of the wavelengths of the infrared radiation emitted then depends on said wavelength and on the distance D, and in particular on the difference in potential applied between the two electrodes.

It is thereby possible to modulate the emission amplitude of the infrared source 100 by a simple mechanical displacement (in other words by modification of the distance D). More specifically, the modification of the distance D is executed by application of a difference in electrostatic potential applied between the first electrode 410 and the second electrode 420.

This effect is particularly advantageous, since electrostatic activation has a sufficient dynamic to realise a modulation of the emissivity of the infrared radiation source at frequencies above ten or so Kilohertzs, and which can potentially reach a Megahertz.

The infrared radiation source 100 according to the present invention may then be implemented in a gas detector operating on the principle of photoacoustic detection, in particular for the detection of a gas having an absorption at a wavelength of interest, noted $\lambda_0$.

Thus, the distance at zero potential $D_0$ may, for example, be the distance for which the radiation at the wavelength of interest $\lambda_0$ emitted by the rear face 220 interferes in a destructive manner with the radiation emitted by the front face 210.

Figure 6A:
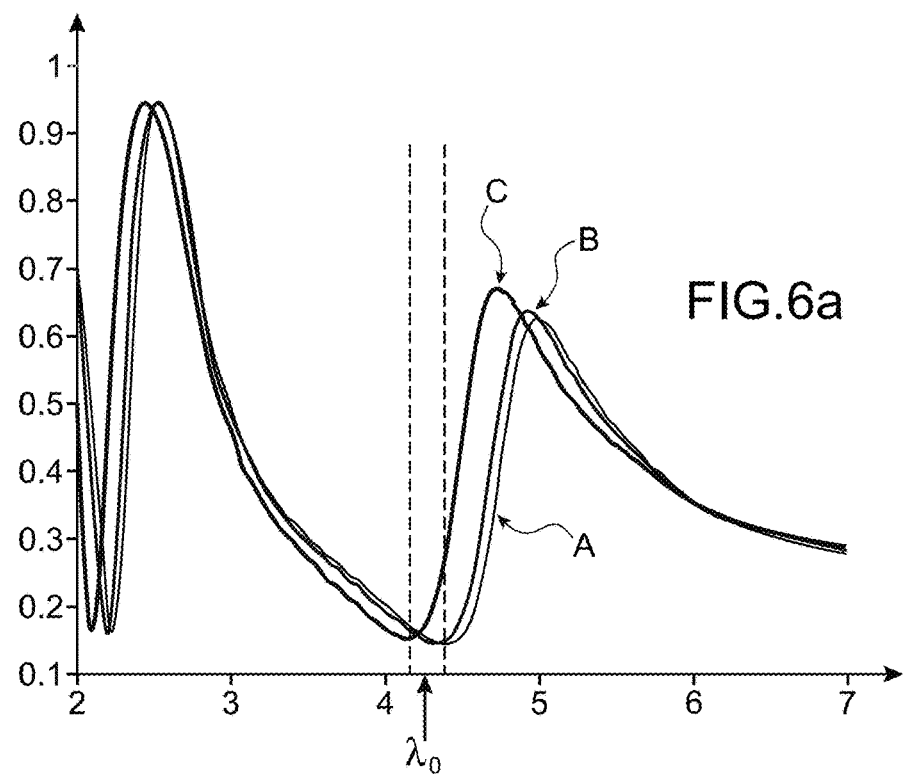
FIGS. 6a and 6b are graphic representations of the emissivity (along the vertical axis) of the infrared radiation source for different emission angles with respect to a direction normal to said membrane (curve A at 0°, curve B at +/−10°, and curve C at +/−20°), the emissivity being given as a function of the wavelength (along the horizontal axis); in particular.

For example, the gas to detect may be carbon dioxide ($CO_2$) that has an absorption at the wavelength of interest $\lambda_0=4.26$ μm. The distance at zero potential $D_0$ is then advantageously equal to 2.1 μm. As illustrated in FIG. 6*a*, the infrared radiation source has an emissivity dip at the wavelength $\lambda_0$ due to destructive interferences. The displacement of the membrane by 0.25 μm at a distance $D_1$=1.85 μm by application of a difference in electrostatic potential between the two electrodes makes it possible to maximise the emissivity of the membrane at the wavelength $\lambda_0$ (FIG. 6b) thanks to constructive interferences. The oscillation of the membrane between two positions corresponding to the distances $D_0$ and $D_1$ at a frequency above 10 kHz may then advantageously be used for the photoacoustic detection of a gas, and in particular $CO_2$.

The infrared radiation source may also be provided with a band pass filter.

The band pass filter, from the moment that the infrared radiation source is implemented in a photoacoustic detection device, may have a narrow band width, for example 0.2 μm wide so as to make the detector selective to a particular gas. For example, for a wavelength of interest $\lambda_0$=4.26 μm, the filter may have the band width 4.16 μm-4.36 μm.

The band pass filter may also, for other applications such as infrared spectroscopy, have a wider band width.

Figure 6B:
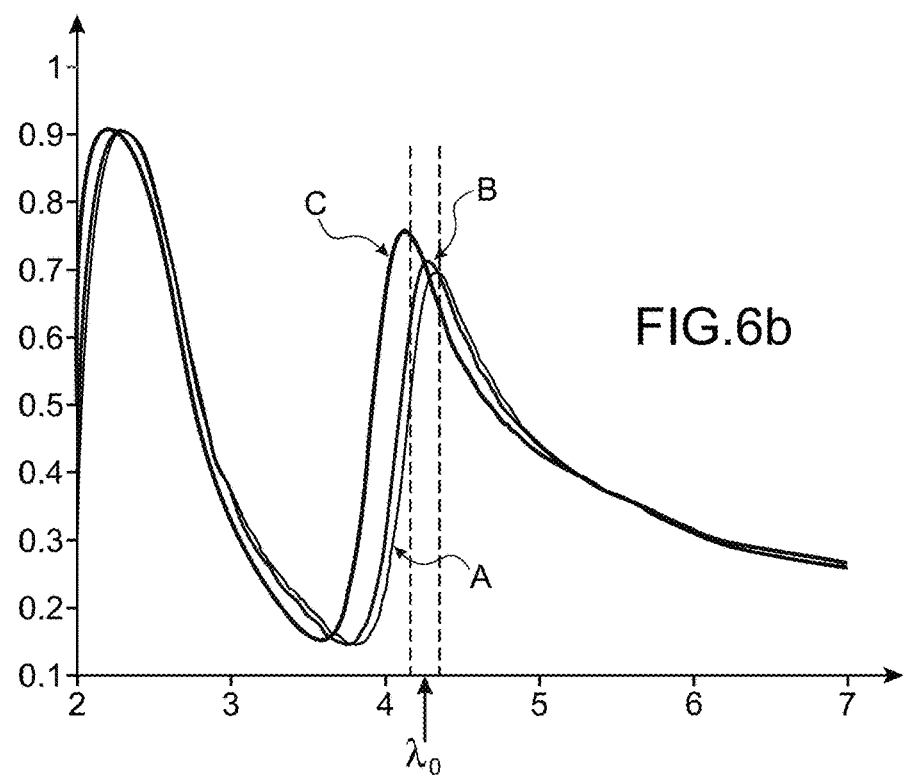

The Inventors have also demonstrated by digital simulation that the modulation of the emissivity spectrum of the membrane is effective in a cone of 40° with respect to the normal of the surface of said membrane (FIGS. 6a and 6b)

The invention also relates to a second embodiment which differs from the first embodiment in that the second electrode 430 wholly covers the rear face 220, advantageously the second electrode is made of conductive transparent oxide. According to this embodiment, and unlike the first embodiment, the whole of the front face 210 and the rear face 220 are emissive. "Transparent" is taken to mean a conductive transparent oxide having a coefficient of extinction k, at the wavelengths involved, below 0.25.

Figure 7:
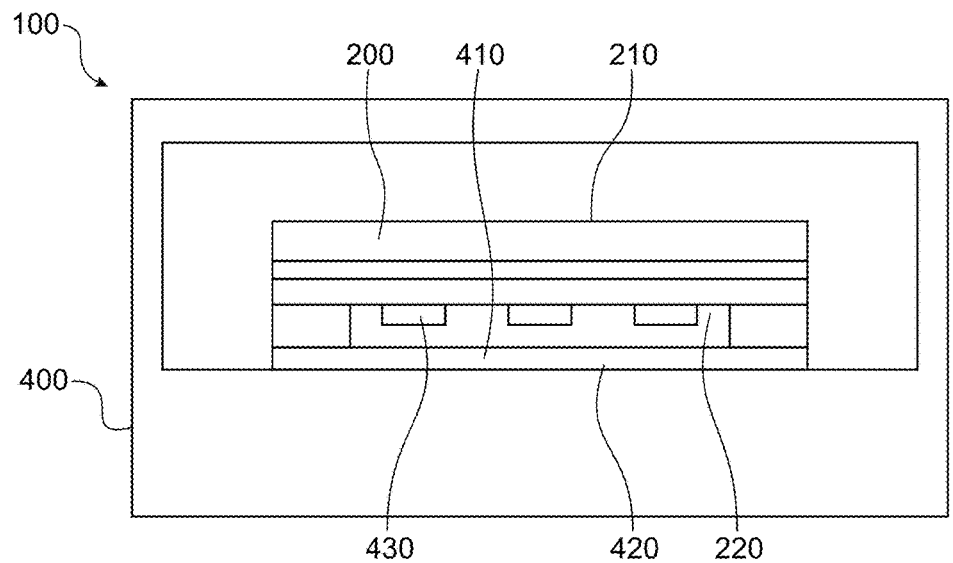
FIG. 7 is a schematic representation of the infrared source according to the present invention arranged in a hermetic enclosure.

According to one or the other of the two embodiments, the support 400 may be a hermetically sealed enclosure, inside of which the membrane is arranged, and of which the environment is maintained at a pressure below $10^{-2}$ mbars, preferentially comprised between $10^{-3}$ mbar and $10^{-2}$ mbar (FIG. 7).

The implementation of the hermetically sealed enclosure makes it possible to limit losses by thermal conduction in air.

The enclosure may advantageously be made of a material transparent to infrared radiation, for example silicon.

Furthermore, the second electrode 420 may comprise a trap or getter adapted, from the moment that it is heated, to trap at least in part gaseous species capable of being present in the enclosure.

In general, such a trap is implemented during the encapsulation of the membrane in a hermetically sealed enclosure (also called "packaging" step), in order to ensure a vacuum in said enclosure and thereby limit losses of infrared radiation capable of being emitted by the membrane.

However, at the end of the "packaging" step, the trap, more specifically its surface, is not saturated. Indeed, the gaseous species trapped at the level of the surface of the trap migrate under the effect of temperature into the volume of the trap (in the mass of said trap) such that the surface of the latter is regenerated. In other words, the trap may still absorb gaseous species from the moment that means are implemented so that it is heated to a temperature, designated activation temperature.

In this respect, the vacuum in the hermetic enclosure can degrade (increase in pressure) during operation of the membrane. For example, an increase in the pressure in the enclosure may result from the desorption of gaseous species at the level of the membrane 200, in particular when the latter is heated to emit an infrared radiation. This increase in pressure inside the enclosure degrades the thermal efficiency of the infrared radiation source 100. The implementation of the trap makes it possible to respond to this problem.

Indeed, according to the present invention, when the membrane 200 is heated to produce an infrared radiation, the second electrode 430 provided with the trap, which is located near to said electrode, also sees its temperature increase to a temperature above the activation temperature of the trap. In other words, the heating of the membrane makes it possible to heat the trap continuously such that said trap absorbs the gaseous species capable of being desorbed by the membrane. Thus the vacuum in the enclosure may be maintained at a level compatible with the requirements in terms of thermal and/or infrared losses.

Advantageously a second electrode 420 made of titanium and/or zirconium forms a trap for the gaseous species.

Indeed, both titanium and zirconium are choice materials for forming the second electrode 420. These elements may advantageously play the role of pump (or micro-pump), and thereby absorb, at least in part, species capable of being desorbed by the membrane 200. The infrared radiation source according to the present invention may be implemented for the detection of gas by infrared spectroscopy, in particular for the detection of several gases without necessarily having to resort to a filter but while making use of the modulation of the emissivity of the infrared source.

The invention also relates to a device for detecting gas by infrared spectroscopy.

The manufacture of the infrared source 200 according to the present invention implements standard micro-manufacturing steps known to those skilled in the art.

Figure 8A:
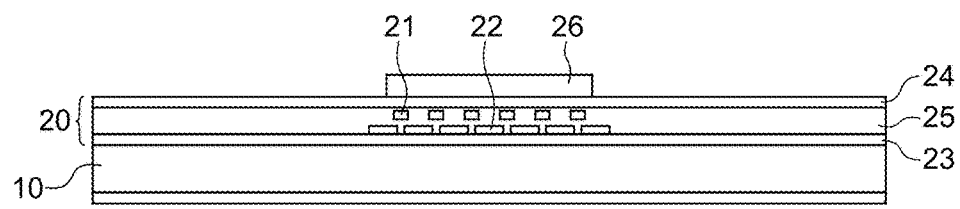
FIGS. 8a to 8e are schematic representations of a method for manufacturing the modular infrared radiation source according to the present invention.

A first manufacturing step 1) illustrated in FIG. 8a comprises the formation of a stack 20 on a support substrate 10, for example a support substrate made of silicon.

The stack 20 is in particular intended to form the membrane 200.

In this respect, the stack may comprise a heating element 21 intended to heat an emissive layer 22, both intercalated between two layers made of a dielectric material 23 and 24, for example silicon dioxide. In addition, the heating element 21 and the emissive layer 22 may be embedded in another dielectric layer 25, for example made of silicon nitride.

The first step 1) also comprises the formation of an electrode 26 (second electrode according to the present invention) directly in line with the heating element 21 and the emissive layer 22.

The different steps of formation of the stack 20 call upon micro-manufacturing techniques known to those skilled in the art and are not described in the present invention.

Figure 8B:
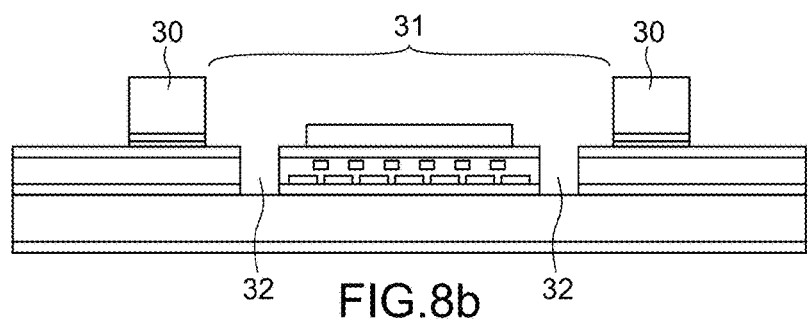

The manufacturing method comprises a second step 2) illustrated in FIG. 8b.

The second step 2) comprises the formation of a first bonding structure 30, made for example of gold and chromium, and delimiting a region of membrane 31 inside of which is located the membrane. This step may involve one or more metal depositions (for example by evaporation) as well as photolithography/etching steps.

The second step 2) further comprises the formation of a trench 32 traversing the stack 20, and defining the membrane at the level of the region of membrane 31. The trench 32 may be formed via an etching, for example a dry etching.

Figure 8C:
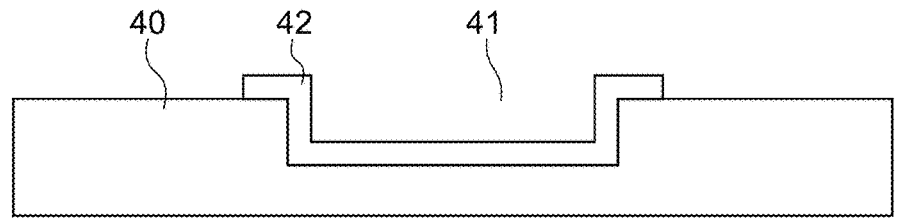

A third step 3), illustrated in FIG. 8c, may next be executed.

The third step comprises the formation of a cavity 41, for example by dry etching, along one face of a second support substrate 40. According to this third step, the cavity 41 is also lined with an electrode 42, designated first electrode according to the present invention.

Figure 8D:
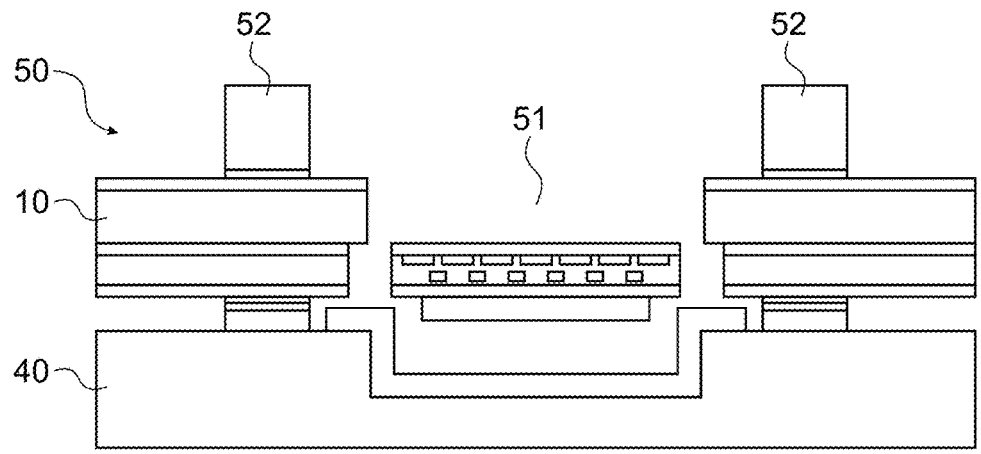

The third step 3) is then followed by a fourth step 4) of assembling the support substrate 10 and the second support substrate 40 (FIG. 8*d*) to form a first assembly 50. The assembling is executed so as to place in correspondence (or facing), the first and second electrodes. A hermetic sealing between the support substrate 10 and the second support substrate 40 is then ensured by the first bonding structure 30.

The fourth step 4) further comprises the formation of a through opening 51 at the level of the support substrate 10 intended to free the membrane. The formation of the through opening 51 may be preceded by a thinning of the support substrate 10 by mechanical abrasion for example.

A second bonding structure 52 is also formed, directly in line with the first bonding structure 30, on a free face of the first assembly 50 at the level of the support substrate 10. In particular, the second bonding structure surrounds the through opening 51.

Figure 8E:
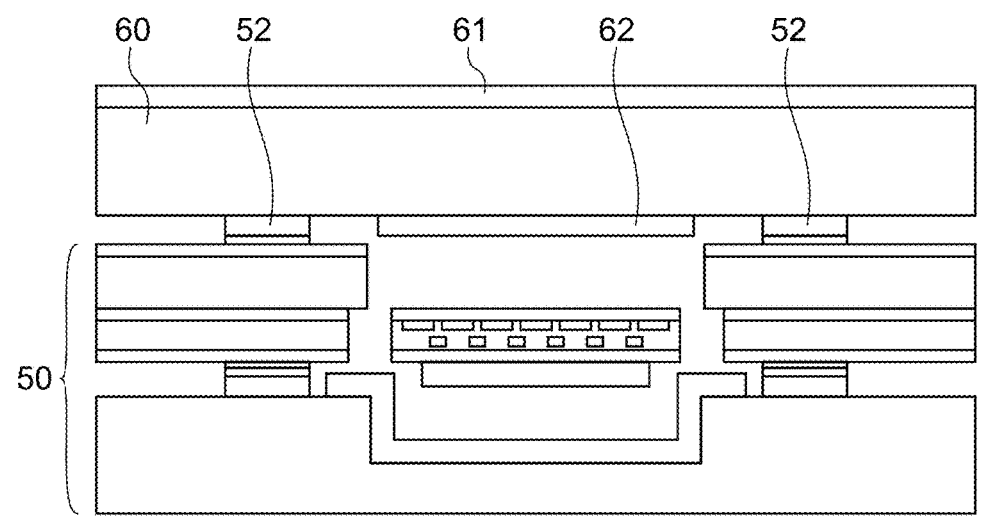

Finally, the manufacturing method comprises a fifth step represented in FIG. 8*e* of formation of a cover 60 intended to hermetically enclose the membrane in an enclosure.

The fifth step thus comprises the bonding of the cover 60 covering the through opening 51. The hermetic sealing of the cover 60 is ensured by the second bonding structure 52. The cover 60 may also be provided with antireflective layers 61 and 62 on one and/or the other of its faces.

The pressure of the cavity thereby formed may be controlled during the step of bonding of the cover, for example by thermally activating a trap arranged in the cavity. As specified in the present description, the second electrode may comprise the trap, in particular said second electrode may be made of a trap material, for example titanium and/or zirconium.

REFERENCES

[1] Pierre Barritault et al., "*Mid-IR source based on a free-standing microhotplate for autonomous $CO_2$ sensing in indoor-applications*", Sensors and Actuators A, 172, p. 379-385, (2011).

The invention claimed is:
1. A modular infrared radiation source, comprising:
a support provided with a flat wall;
a membrane comprising a front face and a rear face being essentially parallel to each other, the membrane being configured to emit infrared radiation by the front face and the rear face, and being maintained in suspension with respect to the support, the rear face facing the flat wall at a distance therefrom, the flat wall being configured to reflect infrared radiation; and
electrostatic actuator comprising a first electrode and a second electrode arranged facing each other, and being configured to vary the distance by application of a difference in electrostatic potential between the first electrode and the second electrode,
wherein the membrane and the electrostatic actuator are arranged such that, for each wavelength, infrared radiation emitted by the rear face is reflected by the flat wall, passes through the membrane from the rear face to the front face, and interferes with infrared radiation emitted by the front face.
2. The modular infrared radiation source according to claim 1, wherein the membrane further comprises an emissive layer configured to, when traversed by a current, heat up and emit infrared radiation.
3. The modular infrared radiation source according to claim 2, wherein the membrane further comprises, from the front face to the rear face, a front dielectric layer, the emissive layer, and a rear dielectric layer.
4. The modular infrared radiation source according to claim 1,
wherein the flat wall forms the first electrode,
wherein the second electrode covers the rear face, and
wherein the second electrode is at least partially transparent to infrared radiation emitted by the membrane.
5. The modular infrared radiation source according to claim 4, wherein the second electrode is cut out such that the second electrode covers the rear face according to a coverage factor comprised between 40% and 60%.
6. The modular infrared radiation source according to claim 5, wherein the second electrode has at least one shape selected from among a grid, a circular spiral, a rectangular spiral, and a coil.
7. The modular infrared radiation source according to claim 5, wherein the second electrode comprises a metal species comprising at least one element selected from among copper, aluminium, tungsten, gold, platinum, silver, palladium, tantalum, and molybdenum.
8. The modular infrared radiation source according to claim 4, wherein the second electrode wholly covers the rear face, and is made of conductive transparent oxide.
9. The modular infrared radiation source according to claim 1, wherein the support is a hermetically sealed enclosure, inside of which the membrane is disposed and an environment is maintained at a pressure below $10^{-2}$ mbars.
10. The modular infrared radiation source according to claim 9, wherein at least one of the first electrode and the second electrode comprises a trap configured to, when heated, at least partially trap a gaseous species if present in the hermetically sealed enclosure, and comprises at least one element selected from among titanium and zirconium.
11. The modular infrared radiation source according to claim 1, further comprising a band pass filter configured to filter emitted infrared radiation.
12. A photoacoustic gas detection device, comprising the modular infrared radiation source according to claim 1.
13. A device for detecting gas by infrared spectroscopy, comprising the modular infrared radiation source according to claim 1.
14. A method for manufacturing an infrared radiation source, the method comprising:
a) forming a membrane comprising a front face and a rear face being essentially parallel to each other, the membrane being configured to emit infrared radiation by the front face and the rear face, and being maintained in suspension with respect to a support, the rear face facing the flat wall at a distance therefrom, the flat wall being configured to reflect infrared radiation; and
b) forming an electrostatic actuator comprising a first electrode and a second electrode arranged facing each other, and being configured to vary the distance by application of a difference in electrostatic potential between the first electrode and the second electrode,
wherein the membrane and the electrostatic actuator are arranged such that, for each wavelength, infrared radiation emitted by the rear face is reflected by the flat wall, passes through the membrane from the rear face to the front face, and interferes with infrared radiation emitted by the front face.

15. The method according to claim 14, wherein step a) further comprises forming a stack on a first face of a first support substrate, the stack being configured to fotlir the membrane.

16. The method according to claim 15, wherein the first support substrate is assembled with a second support substrate to form a hermetic assembly, the second support substrate comprising a cavity of which a bottom thereof forms the flat wall, the flat wall being lined with the first electrode.

17. The method according to claim 16, wherein the hermetic assembly is followed by a step of forming a through opening in the first support substrate from a second face of the first support substrate opposite to the first face of the first support substrate, the step of forming freeing the membrane.

18. The method according to claim 17, wherein step b) further comprises forming the second electrode so as to cover the membrane.

19. The method according to claim 18, further comprising forming a cover covering the through opening by the second face of the first support substrate.

\* \* \* \* \*